(12) United States Patent
Greenberg et al.

(10) Patent No.: US 9,180,296 B2
(45) Date of Patent: *Nov. 10, 2015

(54) METHOD AND SYSTEM FOR PROVIDING STIMULATION INPUTS TO A VISUAL PROSTHESIS IMPLANT

(71) Applicant: Second Sight Medical Products, Inc., San Fernando, CA (US)

(72) Inventors: Robert J Greenberg, Los Angeles, CA (US); Arup Roy, Valencia, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/101,178

(22) Filed: Dec. 9, 2013

(65) Prior Publication Data
US 2014/0100629 A1 Apr. 10, 2014

Related U.S. Application Data

(62) Division of application No. 13/538,987, filed on Jun. 29, 2012, now Pat. No. 8,620,443, and a division of application No. 12/114,557, filed on May 2, 2008, now Pat. No. 8,239,035.

(60) Provisional application No. 60/928,407, filed on May 8, 2007.

(51) Int. Cl.
| A61N 1/36 | (2006.01) |
| A61N 1/05 | (2006.01) |
| A61N 1/372 | (2006.01) |
| G06K 9/46 | (2006.01) |
| G06T 7/00 | (2006.01) |

(52) U.S. Cl.
CPC .......... *A61N 1/36046* (2013.01); *A61N 1/3605* (2013.01); *A61N 1/37247* (2013.01); *G06K 9/4661* (2013.01); *G06T 7/0012* (2013.01)

(58) Field of Classification Search
USPC ...................................... 607/54–53
See application file for complete search history.

(56) References Cited

U.S. PATENT DOCUMENTS

| 4,573,481 | A | 3/1986 | Bullara |
| 4,628,933 | A | 12/1986 | Michelson |
| 4,837,049 | A | 6/1989 | Byers et al. |
| 5,109,844 | A | 5/1992 | de Juan, Jr. et al. |
| 5,215,088 | A | 6/1993 | Normann et al. |
| 5,935,155 | A | 8/1999 | Humayun et al. |
| 6,400,989 | B1 | 6/2002 | Eckmiller |
| 6,458,157 | B1 | 10/2002 | Suaning |
| 8,239,035 | B2 * | 8/2012 | Roy et al. .......................... 607/54 |
| 2002/0010496 | A1 * | 1/2002 | Greenberg et al. .............. 607/54 |
| 2002/0091421 | A1 | 7/2002 | Greenberg et al. |
| 2006/0110008 | A1 * | 5/2006 | Vertegaal et al. .............. 382/103 |
| 2007/0073359 | A1 * | 3/2007 | McClure et al. ................. 607/54 |
| 2007/0255343 | A1 | 11/2007 | McMahon et al. |

FOREIGN PATENT DOCUMENTS

WO    WO 01/91852 A    12/2001

* cited by examiner

*Primary Examiner* — Carl H Layno
*Assistant Examiner* — Jon Eric C Morales
(74) *Attorney, Agent, or Firm* — Scott B. Dunbar

(57) ABSTRACT

Stimulation inputs are provided to a visual prosthesis implant. The images captured by a video decoder are received and digitized to provide a plurality of video frames; integrity of the video frames is checked, the checked video frames are filtered, and the filtered video frames are converted to stimulation inputs. A similar system is also disclosed.

9 Claims, 4 Drawing Sheets

METHOD AND SYSTEM FOR PROVIDING STIMULATION INPUTS TO A VISUAL PROSTHESIS IMPLANT

CROSS REFERENCE TO RELATED APPLICATIONS

This application is a divisional application of U.S. patent application Ser. No. 13/538,987, Filed Jun. 29, 2012, now U.S. Pat. No. 8,620,443, for Method and System for Providing Stimulation Inputs to a Visual Prosthesis Implant which is a divisional application of U.S. patent application Ser. No. 12/114,557, filed May 2, 2008, now U.S. Pat. No. 8,239,035, for Method and System for Providing Stimulation Inputs to a Visual Prosthesis Implant, which claims priority to U.S. Provisional Application 60/928,407 filed on May 8, 2007 and U.S. Provisional Application 60/928,440 filed on May 8, 2007, the contents of both of which are incorporated herein by reference in their entirety. This application may also be related to U.S. Pat. No. 7,957,811, for Spatial Mapping for a Visual Prosthesis, filed May 2, 2008, the contents of which are also incorporated by reference in their entirety.

STATEMENT OF GOVERNMENT INTEREST

This invention was made with government support under grant No. R24EY12893-01, awarded by the National Institutes of Health. The government has certain rights in the invention.

FIELD

The present disclosure relates to operation of visual prostheses implants. More in particular, it relates to a method and system for providing stimulation inputs to a visual prosthesis implant.

SUMMARY

According to a first aspect, a method for providing stimulation inputs to a visual prosthesis implant is provided, comprising: a) receiving images captured by a video decoder; b) digitizing the images to provide a plurality of video frames; c) checking integrity of the video frames to provide checked video frames; d) filtering the checked video frames to provide filtered video frames; and e) converting the filtered video frames to stimulation inputs for the visual prosthesis implant.

According to a second aspect, a system for providing stimulation inputs to a visual prosthesis implant is provided, comprising: a receiver to receive images captured by a video decoder; a digitizer to digitize the received images to provide a plurality of video frames; a video input handler to check integrity of the video frames to provide checked video frames; a video filter processor to filter the checked video frames to provide filtered video frames; and a telemetry engine video manager to convert the filtered video frames to stimulation inputs for the visual prosthesis implant.

According to another aspect of the present disclosure, an improved method is provided, where a visual prosthesis is operated by way of downloadable stimulation maps to control neural stimulation based on a predetermined best fit for an individual patient.

Further aspects of the present disclosure are provide in the written specification, drawings and claims of the present application.

DETAILED DESCRIPTION

Figure 1:
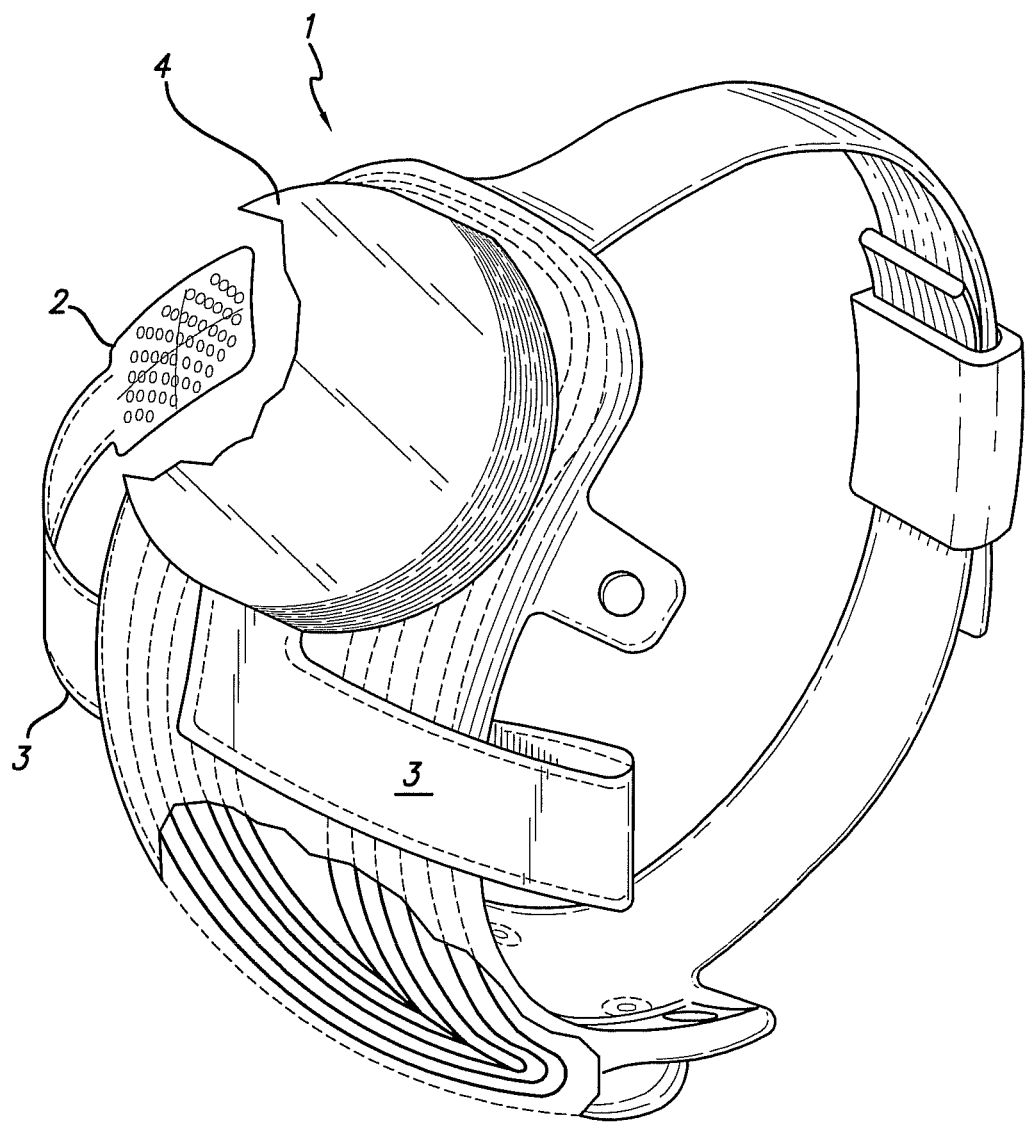
FIGS. 1 and 2 show a retinal stimulation system
Figure 2:
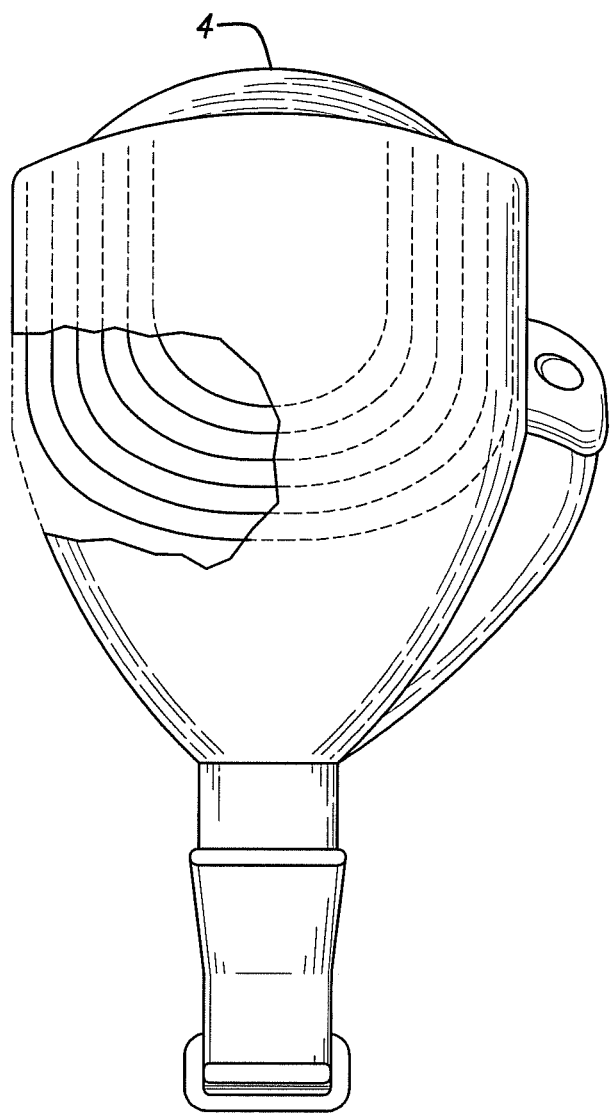

A Retinal Stimulation System, disclosed in U.S. application Ser. No. 11/207,644, filed Aug. 19, 2005 for "Flexible Circuit Electrode Array" by Robert J. Greenberg, et, al. incorporated herein by reference, is intended for use in subjects with retinitis pigmentosa. FIG. 1 and FIG. 2 show a Retinal Stimulation System (1) wherein a patient/subject is implanted with a visual prosthesis. Reference can also be made to FIGS. 1-5 of U.S. application Ser. No. No. 11/796,425, filed Apr. 27, 2007 for "Visual Prosthesis Fitting", also incorporated herein by reference in its entirety.

The Retinal Stimulation System (1) is an implantable electronic device containing electrode array (2) that is electrically coupled by a cable (3) that pierces sclera of the subject's eye and is electrically coupled to an electronics package (4), external to the sclera. The Retinal Stimulation System (1) is designed to elicit visual percepts in blind subjects with retinitis pigmentosa.

Figure 3:
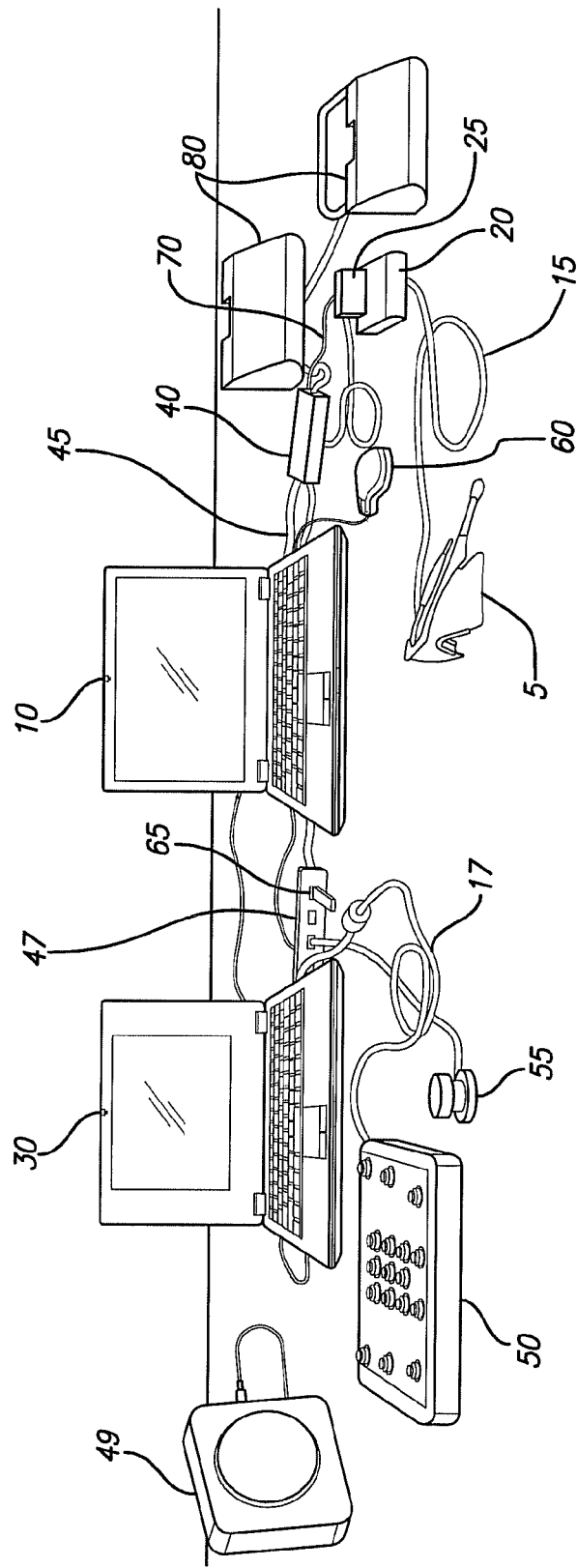
FIG. 3 shows components of a fitting system.

Referring to FIG. 3, a Fitting System (FS) may be used to configure and optimize the visual prosthesis (3) of the Retinal Stimulation System (1).

The Fitting System may comprise custom software with a graphical user interface (GUI) running on a dedicated laptop computer (10). Within the Fitting System are modules for performing diagnostic checks of the implant, loading and executing video configuration files, viewing electrode voltage waveforms, and aiding in conducting psychophysical experiments. A video module can be used to download a video configuration file to a Video Processing Unit (VPU) (20) and store it in non-volatile memory to control various aspects of video configuration, e.g. the spatial relationship between the video input and the electrodes. The software can also load a previously used video configuration file from the VPU (20) for adjustment.

The Fitting System can be connected to the Psychophysical Test System (PTS), located for example on a dedicated laptop (30), in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Any time stimulation is sent to the VPU (20), the stimulation parameters are checked to ensure that maximum charge per phase limits, charge balance, and power limitations are met before the test stimuli are sent to the VPU (20) to make certain that stimulation is safe.

Using the psychophysics module, important perceptual parameters such as perceptual threshold, maximum comfort level, and spatial location of percepts may be reliably measured.

Based on these perceptual parameters, the fitting software enables custom configuration of the transformation between video image and spatio-temporal electrode stimulation parameters in an effort to optimize the effectiveness of the retinal prosthesis for each subject.

The Fitting System laptop (10) is connected to the VPU (20) using an optically isolated serial connection adapter (40).

Because it is optically isolated, the serial connection adapter (40) assures that no electric leakage current can flow from the Fitting System laptop (10).

As shown in FIG. 3, the following components may be used with the Fitting System according to the present disclosure. A Video Processing Unit (VPU) (20) for the subject being tested, a Charged Battery (25) for VPU (20), Glasses (5), a Fitting System (FS) Laptop (10), a Psychophysical Test System (PTS) Laptop (30), a PTS CD (not shown), a Communication Adapter (CA) (40), a USB Drive (Security) (not shown), a USB Drive (Transfer) (not shown), a USB Drive (Video Settings) (not shown), a Patient Input Device (RF Tablet) (50), a further Patient Input Device (Jog Dial) (55), Glasses Cable (15), CA-VPU Cable (70), CFS-CA Cable (45), CFS-PTS Cable (46), Four (4) Port USB Hub (47), Mouse (60), LED Test Array (80), Archival USB Drive (49), an Isolation Transformer (not shown), adapter cables (not shown), and an External Monitor (not shown).

The external components of the Fitting System according to the present disclosure may be configured as follows. The battery (25) is connected with the VPU (20). The PTS Laptop (30) is connected to FS Laptop (10) using the CFS-PTS Cable (46). The PTS Laptop (30) and FS Laptop (10) are plugged into the Isolation Transformer (not shown) using the Adapter Cables (not shown). The Isolation Transformer is plugged into the wall outlet. The four (4) Port USB Hub (47) is connected to the FS laptop (10) at the USB port. The mouse (60) and the two Patient Input Devices (50) and (55) are connected to four (4) Port USB Hubs (47). The FS laptop (10) is connected to the Communication Adapter (CA) (40) using the CFS-CA Cable (45). The CA (40) is connected to the VPU (20) using the CA-VPU Cable (70). The Glasses (5) are connected to the VPU (20) using the Glasses Cable (15).

Video Configuration Information

Video processing can be configured using a collection of settings known as video configuration information. This information can be dynamically set by the host. It includes a spatial map (190), a brightness map (230), timing profiles, and Image Presentation Rate/Stimulation Frequency (210) and zoom settings. See also FIG. 4.

The spatial map (190) is used by the video filters when processing the raw video image. The spatial map can contain one pixel location for every electrode and assume a 12×20 raw video image. A possible application programming interface (API) can be defined as follows:

```
#define ELECTRODE_NUM (60)
typedef struct {
    unsigned short columnPosition;   // column     0 - 19
    unsigned short rowPosition;      // row 0 - 11
} pixelCoordinate;
pixelCoordinate spatialMap[ELECTRODE_NUM];
```

The brightness map (230) is used by the telemetry engine video manager (140), later discussed, to translate the filtered video image brightness levels to driver amplitude values. For each brightness level, an electrode can have a unique corresponding driver amplitude value. There can be one driver amplitude range that is used for all electrodes.

```
#define BRIGHTNESS_LEVELS (32)
unsigned short bright-
nessMap[ELECTRODE_NUM][BRIGHTNESS_LEVELS];
    unsigned short globalAmplitudeRange;
```

According to one embodiment of the present disclosure, there are six timing profiles that can be configured. Each electrode associates one of the six profiles with its anodic pulse, and one of the six for its cathodic pulse.

```
#define PROFILE_NUM (6)
typedef struct {
    unsigned short start;
    unsigned short stop;
} profile;
profile timingProfiles[PROFILE_NUM];
typedef struct {
    unsigned short anodicProfile;
    unsigned short cathodicProfile;
} profileChoice;
profileChoice electrodeProfileSelection[ELECTRODE_NUM];
```

As to the video filter settings, the filter processor (130) can be configured to perform a reverse video filter in conjunction with the DoG filter.

```
struct {
    int reverseVideoOn;          // TRUE or FALSE}
```

The Image Presentation Rate/Stimulation Frequency is used to determine how often to present a new video image to the patient. The maximum effective rate can be 30 Hz if a Phillips video decoder is used as decoder (150). The host specifies how many frames to pad between video image frames. It can be configured for faster than 30 Hz, but this means a video frame is repeated.

unsigned short imageFrequencyPadding;

The zoom setting for the video image capture can be set via the keypad.

unsigned short zoomSetting; // zoom in or zoom out

Figure 4:
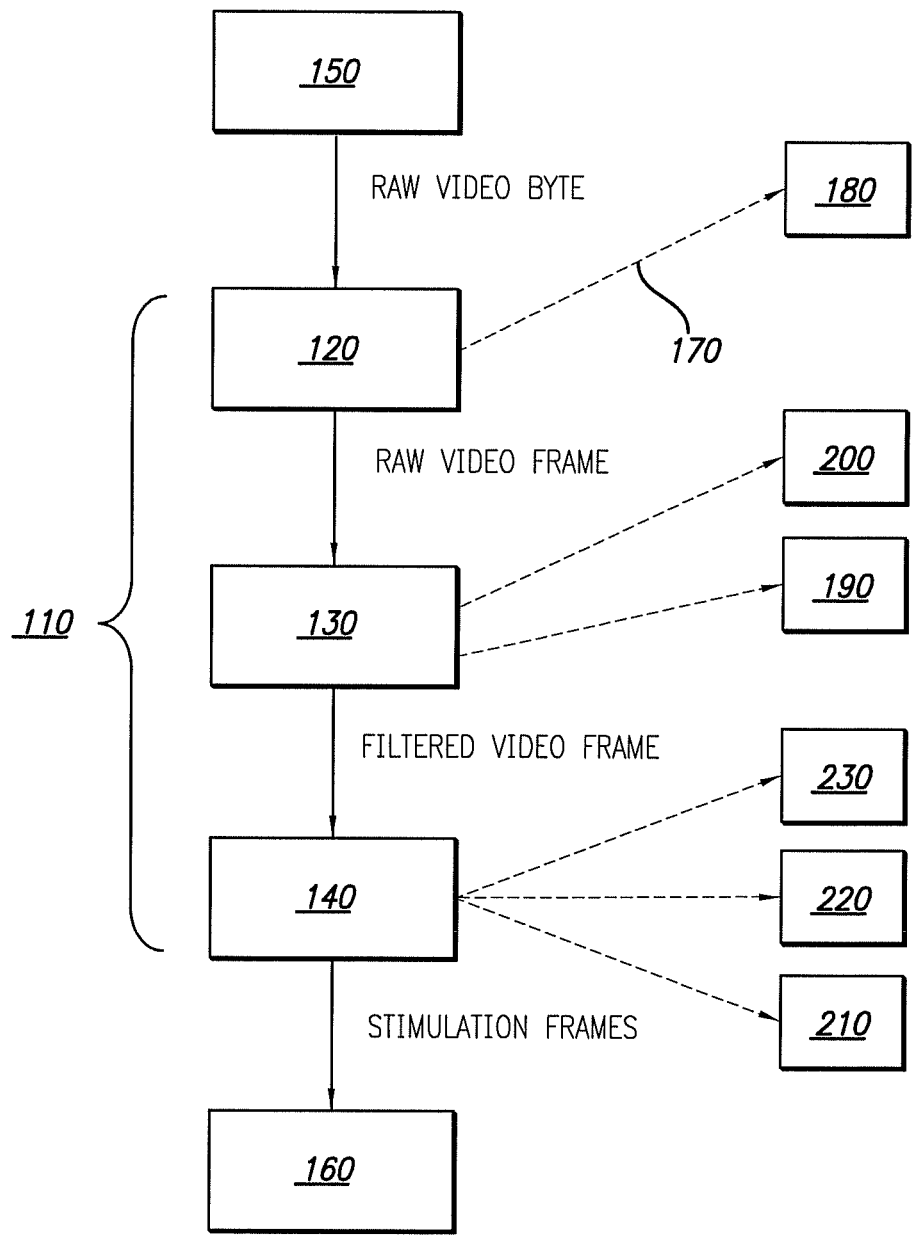
FIG. 4 shows a schematical diagram of components of the system according to the present disclosure.

FIG. 4 shows a schematic view of the system according to the present disclosure. A video decoder (150) is configured to capture images. For example, a Philips video decoder/scaler can be used, which can be configured to capture 12×20 byte images at 30 Hz.

A video engine (110) receives the images captured by the video decoder (150). The video engine (110) comprises three components: a video input handler (120), a video filter processor (130) and a telemetry engine video manager (140).

The video input handler (120) configures the video decoder (150), acquires a raw video input from the video decoder (150), and verifies the integrity of the raw/digitized video frame by checking for frame/line headers. Once a video frame has been successfully acquired by the video input handler (120), the frame is passed to the video filter processor (130). The video input handler (120) can also be responsible for detecting a video overrun (170), following which the system is stopped (180). The video input handler (120) also deals with situations where the video engine (110) does not complete its processing of an individual video frame before a new frame arrives.

The video filter processor (130) receives a raw/digitized video frame from the video input handler (120) and performs filtering to produce a video output image that can be used by the telemetry engine. The video filter processor (130) uses the spatial map (190) configured by the host and additional filter settings (200) to qualify its filtering decisions. In the preferred embodiment, the output of the video filter processor (130) is a 6×10 image, one pixel for each electrode.

The telemetry engine video manager (140) converts the filtered video frame output from the video filter processor (130) into stimulation frames that are sent to the implant (160). The telemetry engine video manager (140) is responsible for accomplishing the image stimulation frequency. The telemetry engine video manager (140) is also associated to an image frequency (210), an output current range (220) and a brightness map (230).

FIG. 4 shows the flow of the video frames through the video engine (110). According to one embodiment of the present disclosure, the video input handler (120), the video filter processor (130) and the telemetry engine video manager (140) are software routines that can run on a digital signal processor (DSP) located between the video decoder (150) and the implant (160). In particular, two DSP/BIOS tasks and one interrupt service routine can share the responsibility of executing the video engine (110). The video input handler (120) and the video filter processor (130) can run under the context of a Video Processing Task routine. Similarly, the telemetry engine video manager (140) can run under the context of an Implant Telemetry Task routine. These two tasks can share the filtered pixel image produced by the video filter processor (130) as a resource.

An application programming interface (API) for establishing communication between the three parts of the video engine (110) will now be described.

filterVideoFrame void filterVideoFrame (unsigned short*videoInputFrame, unsigned short*videoOutputFrame)

Purpose: the video input handler (120) calls this function to invoke the video filter processor (130). The video output frame holds one pixel value for each electrode. The video filter processor (130) takes into account the latest spatial mapping information (200) for each electrode.

| Parameters | | |
|---|---|---|
| Name | Type | Description |
| videoInputFrame | unsigned short * | the raw video input frame |
| videoOutputFrame | unsigned short * | the video output frame |

| Return Value |
|---|
| void | getSpatialMap pixelCoordinate *getSpatialMap(void)

Purpose: the video filter processor (130) calls this function to get the latest spatial map for the electrodes.

| Parameters | | |
|---|---|---|
| Name | Type | Description |
| map | spatialMap * | Holds the latest spatial map information. |

| Return Value |
|---|
| void | isReverseVideoOn int isReverseVideoOn(void)

Purpose: the procedure is called by the video filter processor (130) to determine whether or not reverse video is on.

| Parameters |
|---|
| none |

| Return Value | | |
|---|---|---|
| Name | Type | Description |
| status | int | TRUE, if reverse video is on, FALSE otherwise | getLatestFilteredVideo int getLatestFilteredVideo(unsigned short *filteredVideoFrame)

Purpose: the procedure is called by the telemetry video manager (140) to get the latest filtered video frame.

| Name | Type | Description |
|---|---|---|
| Parameters | | |
| filteredVideoFrame | unsigned short * | the latest filtered video frame |
| Return Value | | |
| status | int | TRUE, if a new frame is available, FALSE otherwise |

The filtering algorithm will now be discussed. In particular, a Difference of Gaussian (DoG) filter is used as the video filter processor (130).

According to an embodiment of the present disclosure, the DoG filter can be determined by 4 parameters:
1) sigmaCenter: the center gaussian variance (in pixel distance)
2) sigmaSurround: the surround gaussian variance (in pixel distance)
3) weightCenter: the center gaussian weight
4) weightSurround: the surround gaussian weight The filter kernel can be defined as:

$$f(x,y) = \text{sigmaCenter} *$$

$$(1/(\text{sigmaCenter}*\text{sqrt}(2*pi)))*\exp(-\tfrac{1}{2}*(x^2+y^2)/(\text{sigmaCenter}^2)) - \text{sigmaSurround}*$$

$$(1/(\text{sigmaSurround}*\text{sqrt}(2*pi)))*\exp(-\tfrac{1}{2}*(x^2+y^2)/(\text{sigmaSurround}^2))$$

A digitized version of the kernel can be obtained by sampling on the continuous kernel. A set of parameters are chosen to help enhancing edge information in the video frame while preserving the relative brightness levels of the individual pixels. By way of example, the parameters that can be used are:

sigmaCenter=0.7
sigmaSurround=2.1
weightCenter=2
weightSurround=−1

The two dimensional convolution of the input rawVideoFrame with the DoG kernel is expensive to compute, especially on the DSP chip of the VPU (20) of FIG. 3. One can observe that, although the DoG kernel is not separable, the underlying gaussian kernels are.

$$f(x,y) = \text{sigmaCenter}*\text{centerGaussianKernel}(x,y)$$

$$-\text{sigmaSurround}*\text{surroundGaussianKernel}(x,y)$$

In view of the separability of the Gaussian kernels, the filtering can be done with a "filter-by-row-then-by-column"

scheme. In addition, this can help take advantage of the hardware acceleration in DSPLIB for one dimension convolution.

Thus a simple algorithm to implement the DoG kernel is:

```
for { each row i of the input image m }
    row_i_of_c1 = convolve( row_i_of_m, center_kernel );
    row_i_of_s1 = convolve( row_i_of_m, surround_kernel );}
for { each column j of c1 }
    column_j_of_c2 = convolve( column_j_of_c1, center_kernel );
end
for { each column j of s1 }
    column_j_of_s2 = convolve( column_j_of_s1, surround_kernel );
end
result = weightCenter * c2 – weightSurround * s2;
```

The result of the DoG filter is an image of the same size as the rawVideoFrame (20×12). The final step of the filter processor (130) is to sample at the locations required in the spatial map. The output will be 60 brightness values, one for each electrode.

Video Stimulation Mode

In this mode, the video decoder (150) is configured to capture a raw pixilated image from the NTSC source based on the current zoom setting. Video data for stimulation that has been indicated as invalid should not be used. This will occur when the camera is disconnected or if communications problem occur with the video decoder (150).

An image processing filter will be used to process the raw pixel image. The final filtered image should always be a 6×10 grayscale pixilated image. To compensate for possible non-linear spatial mapping of electrode response to electrical stimulation, an arbitrary pixel to electrode array space mapping can be used, to map each of the 60 electrodes to a particular image pixel. This mapping can be modified by the user.

Further, brightness mapping to map for each electrode the pixel intensity of the electrode to current amplitude can be used. This mapping can be modified by the user.

Mapping of Video to Electrodes

The output mapping can be alterable. Each of the individual pixels can have a locus set and saved in the PC program. This locus shall be mapped to the video image pixel. The video image shall determine a pixel luminance value for this pixel.

The mapping of luminance to pixel electrical stimulation parameters shall allow the PC program to set a mapping of luminance to pixel electrical stimulation parameters through providing a mapping (constant, linear or exponential) of the following variables to electrical stimulation parameters through a range settable for each pixel and based on how many electrodes are presently on.

Amplitudes
Pulse Width

The following electrode driver variables shall not be controlled by luminance, but set to values by the PC program Oscillator Offset
Interphase Delay
Polarity
Number of Pulses
Frequency The user shall have the option of programming a shorting command during times in which the electrode is not stimulating.

Mapping of the Luminance vs. the Electrode Stimulation

According to a further embodiment of the disclosure, the system can contain the following luminance vs. electrode stimulation mapping choices:

Location Mapping
Amplitude Mapping
Pulse width Mapping

For each electrode, the applied parameters can be:

X-location (0 to 15)
Y-location (0 to 15)
Minimum amplitude
Maximum amplitude
Amplitude range
Amplitude transform type (constant, linear, or exponential)
Minimum pulse width
Maximum pulse width
Pulse width range
Pulse width transform type (constant, linear, or exponential)

The pixel location can relate to a 4 by 4 output map (16 pixels), and can be limited for x and y values between and including 0 and 15. The PC settable value of BinaryFilterPoint can be used as a floor for camera illumination. The PC settable value of BinaryRange, which is 0xFF-BinaryFilterPoint, can be used as the range for the camera range.

Three types of amplitude transformation can be provided:
1) Constant: the minimum amplitude value is used
2) Linear: a linear transformation between pixel brightness and amplitude is used, according to the formula (as computed in µA, not clinical units (CU))

$$\text{Amplitude}=(\text{pixelValue}-\text{BinaryFilterPoint})/(\text{BinaryFilterRange})*(\text{Amplitude\_Range})+\text{minimum\_amplitude}.$$

3) Exponential: an exponential transformation between the pixel brightness and amplitude is used, according to the formula (as computed in clinical units (CU), not µA)

$$\text{Amplitude}=(\text{pixelValue}-\text{BinaryFilterPoint})/(\text{BinaryFilterRange})*(\text{Amplitude\_Range})+\text{minimum\_amplitude}.$$

Three types of pulse width conversions can be provided:
1) Constant: the minimum pulse width is used
2) Linear: a linear transformation between pixel brightness and pulse width is used, according to the formula (the pulse width range and amplitudes are in ms).

$$\text{PulseWidth}=(\text{pixelValue}-\text{BinaryFilterPoint})/(\text{BinaryFilterRange})*(\text{puslewidthRange})+\text{minimum\_pulsewidth}.$$

3) Exponential: an exponential transformation is used in accordance with a factor of 5000×. This value was chosen as it is the value used in the Clarion output range setting. In the following formula, the pulse widths are first converted into clinical units (CUs) using a logarithmic (base 5000) function, and then the range and amplitudes computed in CUs.

$$\text{PulseWidth}=(\text{pixelValue}-\text{BinaryFilterPoint})/(\text{BinaryFilterRange})*(\text{puslewidthRange})+\text{minimum\_pulsewidth}.$$

A current filter can be used to reduce the amount of current that is sent to the patient based on the electrodes that are turned on. Each electrode is compared to a PC settable ON value of each electrode, and a COUNT is made of the number of ON electrodes. Each electrode's clinical units is reduced by a clinical units that is dependent upon COUNT if the remaining current on the electrode is greater than a minimum current settable for each individual electrode.

Multiple Patient Settings

A maximum number of patient setting (e.g., 7) can be established. For each of the 16 electrodes, the applicable parameters as set by any individual patient setting can be:

Minimum amplitude
Maximum amplitude
Amplitude transform type (constant, linear, or exponential)
Minimum Pulse width
Maximum Pulse width
Pulse width transform type (constant, linear, or exponential)
Frequency
Polarity
Oscillator Offset
Delay between Phases
Number of Pulses
Pixel-to-electrode coordinates Each patient setting can have a unique BinaryFilterPoint and corresponding BinaryFilterRange. Each patient setting can have a filter implementation. The system can startup with the current Patient Setting pointing to the first Patient Setting on the list. The PC (e.g., laptop (10) of FIG. 3) should not be able to disable the first Patient Setting on the list. The PC can have the ability to download electrode stimulation parameters to any valid Patient Setting on the VPU.

The PC can have the ability to upload any valid Patient Setting on the VPU for inspection. The PC can have the ability to disable any valid Patient Setting (except the first one) on the VPU. Any valid Patient Setting gets automatically enabled when the PC sets it.

The user can have the ability to scroll through the enabled Patient Settings in a circular fashion. An audible feedback is provided to the user designating which particular Patient Setting (s)he is on. The forward telemetry can complete the ongoing stimulation first with the parameters of the previous Patient Setting. The pulse waveform parameters can then be updated with the parameters from the next scrolled Patient Setting.

The PC can have the ability to set the current Patient Setting to any valid enabled Patient Setting on the list. The PC can have the ability to upload the current Patient Setting on the VPU at any time.

Accordingly, what has been shown are methods and systems for providing stimulation inputs to a visual prosthesis implant. While these methods and systems have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

What is claimed is:

1. A system for providing stimulation inputs to a visual prosthesis implant, comprising:
   a camera providing images to a video decoder;
   a receiver to receive the images captured by the video decoder yielding received images;
   a digitizer to digitize the received images to provide a plurality of video frames;
   a video input handler to check integrity of the video frames to provide checked video frames;
   a video filter processor to filter the checked video frames to provide filtered video frames; and
   a telemetry engine video manager to convert the filtered video frames to stimulation inputs for the visual prosthesis implant.

2. The system of claim 1, wherein the video input handler also detects a video overrun.

3. The system of claim 1, wherein the video filter processor employs spatial mapping.

4. The system of claim 3, wherein the visual prosthesis implant includes a plurality of electrodes and the spatial mapping is employed for each electrode.

5. The system of claim 1, wherein the telemetry engine video manager uses a brightness map.

6. The system of claim 1, wherein the video input handler, the video filter processor and the telemetry engine video manager are in a digital signal processor (DSP), the DSP configured to be connected with the visual prosthesis implant.

7. The system of claim 6, wherein the DSP is located in a video processing unit (VPU).

8. The system of claim 7, wherein the video decoder is configured to be connectable to a camera and wherein the video input handler, the video filter processor and the telemetry engine video manager operate with a connected camera.

9. The system of claim 1, wherein the video decoder is configured to be connectable to a camera and the video input handler, the video filter processor and the telemetry engine video manager operate with a disconnected camera.

* * * * *